United States Patent [19]
Li et al.

[11] Patent Number: 6,127,573
[45] Date of Patent: Oct. 3, 2000

[54] OXIDATON OF PRIMARY ALCOHOLS TO CARBOXYLIC ACIDS WITH A TEMPO CATALYST USING NACLO$_2$ AND NACLO

[75] Inventors: Jing Li; Zhiguo Song, both of Edison; David M. Tschaen, Holmdel; Mangzu Zhao, Edison, all of N.J.

[73] Assignee: Merck & Co., Inc., Rahway, N.J.

[21] Appl. No.: 09/283,936

[22] Filed: Apr. 1, 1999

Related U.S. Application Data

[60] Provisional application No. 60/081,202, Apr. 9, 1998.

[51] Int. Cl.$^7$ .................................................... C07C 51/16
[52] U.S. Cl. .......................... 562/419; 562/409; 562/416; 562/422; 562/490; 562/526; 562/491; 562/493; 562/556; 562/561; 562/609; 562/621
[58] Field of Search .................................... 562/409, 416, 562/419, 422, 490, 491, 493, 526, 556, 561, 609, 621

[56] References Cited

U.S. PATENT DOCUMENTS 5,631,366  5/1997  Lohri et al. .

OTHER PUBLICATIONS

Wovkulich et al.; J. Org. Chem.; vol. 58; p. 832, 1993.
Nooy et al.; Synthesis; p. 1153, 1996.
Ohira, S., Synthetic Communications, vol. 19, pp. 561–564, 1989.
Muller, S., Synlett, pp. 521–522, 1996.
Anelli, P.L., et al., J. Org. Chem., vol. 52(12), pp. 2559–2562.
Dalcanale, E., et al., J. Org. Chem., vol. 51(4), pp. 567–571, 1986.
Zhao, M., et al., J. Org. Chem., vol. 64(7), pp. 2564–2566, 1999.

*Primary Examiner*—Paul J. Killos
*Assistant Examiner*—Robert W. Deemie
*Attorney, Agent, or Firm*—Valerie J. Camara; Mark R. Daniel

[57] ABSTRACT

The present invention relates to a TEMPO-catalyzed oxidation of primary alcohols, RCH$_2$OH to corresponding carboxylic acids, RCOOH in the presence of catalytic in the presence of catalytic amount of NaClO and stoichiometric amount of NaClO$_2$ as an oxidant.

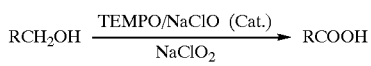

13 Claims, No Drawings

OXIDATON OF PRIMARY ALCOHOLS TO CARBOXYLIC ACIDS WITH A TEMPO CATALYST USING NACLO₂ AND NACLO

This application claims the benefit of U.S. Provisional Application 60/081,202, filed Apr. 9, 1998.

BACKGROUND OF THE INVENTION

Oxidation is one of the most fundamental transformations in organic synthesis and there are numerous methods reported in the literature. (Hudlicky, M. "Oxidations In Organic Chemistry", ACS Monograph No. 186 American Chemical Society Washington D.C. (1990).) However, relatively few methods exist for the oxidation of primary alcohols to the corresponding carboxylic acids. The most commonly used ones are $CrO_3/H_2SO_4$ (Bowden; Heilbron; Jones; Weedon *J. Chem. Soc.,* 1946, 39; Bowers; H.; Jones; L. *J. Chem. Soc.,* 1953, 2548; Millar, J.G.; Oehlschlager, A.C.; Wong, J.W. *J. Org. Chem.* 1983, 48, 4404.), $RuCl_3/H_5IO_6$ (Carlsen, P.H.J.; Katsuki, T.; Martin V.S.; Sharpless, K.B. *J. Org. Chem.* 1981, 46, 3936.) and TEMPO/NaClO (Nooy, A.E.J. de; Besemer, A.C.; Bekkum, H. v. *Synthesis,* 1996, 1153.; Anelli, P.L.; Biffi, C.; Montanari, F.; Quici, S. *J. Org. Chem.* 1987,52, 2559.; Miyazawa, T.; Endo, T.; Shiihashi, S.; Okawara, M. *J. Org. Chem.* 1985, 50, 1332). A two-step process involving Swern oxidation (Mancuso, A.J.; Huang, S-L., Swern, D. *J. Org. Chem.* 1978,43, 2480.; Mancuso, A.J.; Brownfan, D.S.; Swern, D. *J. Org. Chem.* 1979,44, 4148.; Ireland, R.; Norbeck, D. *J. Org. Chem.* 1985,50, 2198.) followed by oxidation of the resulting aldehyde with $NaClO_2$ (Lindgren, B.O.; Nilsson, T. *Acta Chem. Scand.* 1973,27, 888.; Dalcanale, E.; Montanari, F. *J. Org. Chem.* 1986, 51, 567) is another option. All of these procedures have some limitations and disadvantages and new methods for the oxidation of primary alcohols to the carboxylic acids are still desired. (Schroder, M.; Griffith, W.P. *J. Chem. Soc. Chem. Comm.* 1979, 58.; and Paquette, L.A.; Dressel, J.; Pansegrau, P.D. *Tetrahedron Lett.* 1987, 28,4965.)

The present invention relates to an oxidation using sodium chlorite in the presence of a catalytic amount of TEMPO and sodium hypochlorite which converts a primary alcohol to a carboxylic acid. This oxidation method avoids the disposal issues associated with running a Jones oxidation $(CrO_3/H_2SO_4)$ reaction, as well as reducing the epimerization of any α-chiral centers and is a one step procedure. For substrates prone to chlorination with the TEMPO-NaClO protocol, the present invention reduces this problem.

SUMMARY OF THE INVENTION

The present invention discloses a process for preparing a compound of Formula I:

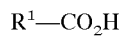

I wherein:
$R^1$ is:
a) H,
b) $C_1-C_8$ alkyl,
c) $C_2-C_8$ alkynyl,
d) $C_3-C_7$ cycloalkyl,
e) aryl,
f) heteroaryl, or
g) heterocyclyl;

$C_1-C_8$ alkyl, $C_2-C_8$ alkynyl, or $C_3-C_8$ cycloalkyl, are unsubstituted or substituted with one, two or three substituents selected from the group consisting of: OH, $CO_2R^4$, Br, Cl, F, I, $CF_3$, $C_1-C_8$ alkoxy, $C_3-C_8$ cycloalkyl, aryl, heteroaryl, heterocyclyl, and $CO(CH_2)_nCH_3$;

aryl is defined as phenyl or naphthyl, which is unsubstituted or substituted with one, two or three substituents selected from the group consisting of: OH, $CO_2R^4$, Br, Cl, F, I, $CF_3$, $C_1-C_8$ alkoxy, $C_1-C_8$ alkyl, $C_2-C_8$ alkynyl, or $C_3-C_8$ cycloalkyl, $CO(CH_2)_nCH_3$, or when aryl is substituted on adjacent carbons they can form a 5- or 6-membered fused ring having one, two or three heteroatoms selected from O, N, and S, this ring is unsubstituted or substituted on carbon or nitrogen with one, two or three substituents selected from the group consisting of: OH, $CO_2R^4$, Br, Cl, F, I, $CF_3$, $C_1-C_8$ alkoxy, $C_1-C_8$ alkyl, $C_2-C_8$ alkenyl, $C_2-C_8$ alkynyl, $C_3-C_8$ cycloalkyl, and $CO(CH_2)_nCH_3$;

heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $C_1-C_8$ alkoxy, $C_1-C_8$ alkyl, $C_2-C_8$ alkynyl, $C_3-C_8$ cycloalkyl, $CO(CH_2)_nCH_3$, and additionally the 5- or 6-membered aromatic ring can be benzofused and unsubstituted or substituted with one, two or three substituents as described above;

heterocyclyl is defined as a 5- or 6-membered, non-aromatic ring containing 1, 2 or 3 heteroatoms selected from O, N and S, which may contain one or two double bonds and which is unsubstituted or substituted with one, two or three substituents selected from the group consisting of: OH, $CO_2R^4$, Br, Cl, F, I, $CF_3$, $C_1-C_8$ alkoxy, $C_1-C_8$ alkyl, $C_2-C_8$ alkynyl, or $C_3-C_8$ cycloalkyl, $CO(CH_2)_nCH_3$, and additionally the 5- or 6-membered ring can be benzofused and unsubstituted or substituted with one, two or three substituents as described above;

n is: 0 to 5;
t is: 0, 1 or 2;
$R^4$ is: H, or $C_1-C_8$ alkyl; or
comprising the following steps:
1) adding to a compound of Formula II in a solvent,

II a solution of phosphate buffer to maintain a pH of about 4.0 to about 8.0;

2) maintaining the phosphate-buffered biphasic mixture of the compound of Formula II at about 0° C. to about 50° C.;

3) adding a catalytic amount of TEMPO to the mixture; and 4) charging the TEMPO/phosphate-buffered biphasic mixture with a solution of sodium chlorite and a catalytic amount of sodium hypochlorite to oxidize to the compound of Formula I.

DETAILED DESCRIPTION OF THE INVENTION

The present invention discloses a process for preparing a compound of Formula I:

$$R^1\text{—}CO_2H$$

I wherein:

$R^1$ is:
a) H,
b) $C_1$–$C_8$ alkyl,
c) $C_2$–$C_8$ alkynyl,
d) $C_3$–$C_7$ cycloalkyl,
e) aryl,
f) heteroaryl, or
g) heterocyclyl;

$C_1$–$C_8$ alkyl, $C_2$–$C_8$ alkynyl, or $C_3$–$C_8$ cycloalkyl, are unsubstituted or substituted with one, two or three substituents selected from the group consisting of: OH, $CO_2R^4$, Br, Cl, F, I, $CF_3$, $C_1$–$C_8$ alkoxy, $C_3$–$C_8$ cycloalkyl; aryl, heteroaryl, heterocyclyl, and $CO(CH_2)_nCH_3$, aryl is defined as phenyl or naphthyl, which is unsubstituted or substituted with one, two or three substituents selected from the group consisting of: OH, $CO_2R^4$, Br, Cl, F, I, $CF_3$, $C_1$–$C_8$ alkoxy, $C_1$–$C_8$ alkyl, $C_2$–$C_8$ alkynyl, or $C_3$–$C_8$ cycloalkyl, $CO(CH_2)_nCH_3$, or when aryl is substituted on adjacent carbons they can form a 5- or 6-membered fused ring having one, two or three heteroatoms selected from O, N, and S, this ring is unsubstituted or substituted on carbon or nitrogen with one, two or three substituents selected from the group consisting of: OH, $CO_2R^4$, Br, Cl, F, I, $CF_3$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, and $CO(CH_2)_nCH_3$;

heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $C_1$–$C_8$ alkoxy, $C_1$–$C_8$ alkyl, $C_2$–$C_8$ alkynyl, $C_3$–$C_8$ cycloalkyl, $CO(CH_2)_nCH_3$, and additionally the 5- or 6-membered aromatic ring can be benzofused and unsubstituted or substituted with one, two or three substituents as described above;

heterocyclyl is defined as a 5- or 6-membered, non-aromatic ring containing 1, 2 or 3 heteroatoms selected from O, N and S, which may contain one or two double bonds and which is unsubstituted or substituted with one, two or three substituents selected from the group consisting of: OH, $CO_2R^4$, Br, Cl, F, I, $CF_3$, $C_1$–$C_8$ alkoxy, $C_1$–$C_8$ alkyl, $C_2$–$C_8$ alkynyl, $C_3$–$C_8$ cycloalkyl, $CO(CH_2)_nCH_3$, and additionally the 5- or 6-membered ring can be benzofused and unsubstituted or substituted with one, two or three substituents as described above;

n is: 0 to 5;
t is: 0, 1 or 2;
$R^4$ is: H, or $C_1$–$C_8$ alkyl; or comprising the following steps:
1) adding to a compound of Formula II in a solvent, $$R^1\text{—}CH_2OH$$

II a solution of phosphate buffer to maintain a pH of about 4.0 to about 8.0;

2) maintaining the phosphate-buffered biphasic mixture of the compound of Formula II at about 0° C. to about 50° C.;

3) adding a catalytic amount of TEMPO to the mixture; and 4) charging the TEMPO/phosphate-buffered biphasic mixture with a solution of sodium chlorite and a catalytic amount of sodium hypochlorite to oxidize to the compound of Formula I.

The process as recited above, wherein the solvent is selected from the group consisting of: acetonitrile, tetrahydrofuran, acetone, tertiary $C_4$–$C_8$-alcohol, diethyl ether, DME (dimethyl ether), diglyme, triglyme, MTBE (methyl t-butyl ether), toluene, benzene, hexane, pentane, dioxane, dichloromethane, chloroform, carbon tetrachloride, or a mixture of said solvents.

The process as recited above, wherein the phosphate buffer comprises an aqueous mixture of NaOH, KOH, $NaH_2PO_4$, $KH_2PO_4$, $Na_2HPO_4$, and $K_2HPO_4$, sufficient to maintain a pH of about 4.0 to about 8.0, and preferably a pH of about 6.5 to about 7.0.

The process as recited above, wherein TEMPO (2,2,6,6-tetramethyl-1-piperidinyloxy, free radical) is used in about 1.0 to about 10.0 mole percent, preferably about 5.0 to about 7.0 mole percent.

The process as recited above, wherein sodium chlorite is used in about 1.0 to about 3.0 equivalents, and preferably about 2.0 equivalents relative to the compound of Formula II.

The process as recited above, wherein sodium hypochlorite is used in about 1.0 to about 7.0 mole percent, preferably about 2.0 to about 5.0 mole percent.

The process as recited above, wherein the reaction temperature is about 0° C. to about 50° C., and preferably about 35° C. to about 40° C.

The process as recited above, wherein the reaction time is up to about 24 hours, and preferably between about 2 and about 4 hours.

It is further understood that the substituents recited above would include the definitions recited below.

The alkyl substituents recited above denote straight and branched chain hydrocarbons of the length specified such as methyl, ethyl, isopropyl, isobutyl, tert-butyl, neopentyl, isopentyl, etc.

Cycloalkyl denotes rings composed of 3 to 8 methylene groups, each of which may be substituted or unsubstituted with other hydrocarbon substituents, and include for example cyclopropyl, cyclobutyl, cyclopentyl, cyclohexyl and 4-methylcyclohexyl.

The alkoxy substituent represents an alkyl group as described above attached through an oxygen bridge.

The aryl substituent represents phenyl and 1-naphthyl or 2-naphthyl, including aryls substituted with a 5- or 6-membered fused ring, such as an unsubstituted and substituted methylenedioxy, oxazolyl, imidazolyl, or thiazolyl ring.

The heteroaryl substituent represents a carbazolyl, furanyl, thienyl, pyrrolyl, isothiazolyl, imidazolyl, isoxazolyl, thiazolyl, oxazolyl, pyrazolyl, pyrazinyl, pyridyl, pyrimidyl, purinyl.

The heterocyclyl substituent represents, oxazolidinyl, thiazolidinyl, thiazolidinyl, oxadiazolyl, or thiadiazolyl.

Each of the above substituents (alkyl, alkynyl, alkoxy, cycloalkyl, aryl, heteroaryl, and heterocyclyl) can be either unsubstituted or substituted as defined within the description.

Recently, in an attempt to oxidize primary alcohols, such as 1m:

1m

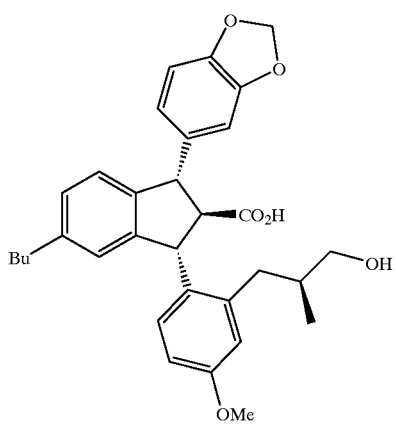

to the corresponding carboxylic acid, we found that $RuCl_3/H_5IO_6$ protocol offered low yield of the desired products. See Carlsen, P.H. et al. *J. Org. Chem.* 1981, 46, 3936. It was probably due to the destruction of electron rich aromatic ring. TEMPO catalyzed oxidation with bleach also gave low yield due to significant chlorination of the aromatic rings. See A.E.J. de Nooy, et al. *Synthesis,* 1996, 1153.; P.L. Anelli, et al. S. *J Org. Chem.* 1987, 52, 2559. and T. Miyazawa, et al. *J. Org. Chem.* 1985, 50, 1332. The synthesis of 1m decribed in Merck Case No. 20127PV, entitled "Oxidation Process Using TEMPO" which is being filed simultaneously with this application.

In order to eliminate the chlorination problem, a few other oxidants ($H_2O_2$, $AcO_2H$, $t-BuO_2H$ etc.) were examined, but no satisfactory results was obtained. Finally, when sodium chlorite ($NaClO_2$) was used as the oxidant, the product were obtained in 70–90% yield. The reaction appeared to be very slow (1–2 %/hour) but generally went to completion overnight (~20 hours). More careful monitoring of the reaction indicated that it was self accelerating process e.g. the conversion was less than 5% after one hour but reached ~90% in only 6 hours. Apparently, some more active species was generated as the reaction progress. Sodium hypochlorite (NaClO, bleach) was believed to be the most likely candidate. Indeed, when 10 mol % of bleach was added to the reaction mixture, the reaction was accelerate dramatically. It reached >50% conversion in one hour and finished in approximately three hours.

SCHEME 1

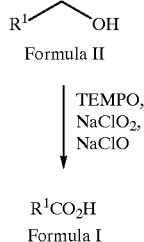

The reaction was then optimized regard to further reduce the chlorination and enhance the safety for scale up. The reaction was faster at lower pH, but it was accompanied by increased chlorination. It was slower at lower temperature as expected, but surprisingly, the chlorination level appeared to be slightly elevated. Increasing the amount of TEMPO and bleach increased the reaction rate, but the TEMPO/NaClO ratio should be >2 to reduce the chances of chlorination. The bleach was added slowly and simultaneously with $NaClO_2$ to the batch at 35° C. to prevent build up of the oxidant and the risk of a run away reaction. It should be noted that mixing of bleach and $NaClO_2$ prior to the addition is not advised since some toxic and potentially explosive chlorine dioxide ($ClO_2$) may be generated.

Next, a number of primary alcohols were oxidized to the carboxylic acids and the results are summarized in Table 1. In general, the reaction were very smooth and the yield were excellent (85–100%). Chiral alcohols 1g, 1j, and 1k were oxidized to the corresponding carboxylic acid without any racemization of the labile chiral centers.

Mostly notably, for substrates prone to chlorination (1c–1h), our new procedure gave much better yields. The most dramatic demonstration of the superiority of our new procedure was revealed in entry 5. When 1e was treated with NaClO and catalytic TEMPO, the desired product was obtained in less than 5% yield. One of the major side product was isolated and identified to be the chlorinated compound 4,

4

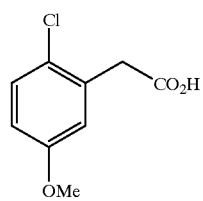

based on NMR studies. On the other hand, our TEMPO/$NaClO_2$ protocol offered essentially quantitative yield of 2e.

TABLE 1
TEMPO Catalyzed Oxidation of Primary Alcohols to Carboxylic Acids
| Substrate | Product | Yield (NaClO$_2$) | Yield (NaClO) |
|---|---|---|---|
| 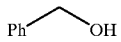 1a | 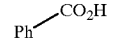 2a | 98% | — |
| 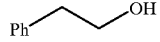 1b | 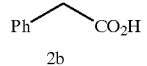 2b | 100% | — |
| 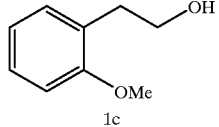 1c | 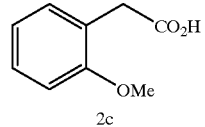 2c | 99% | 65% |
| 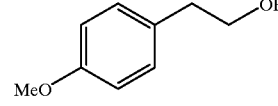 1d | 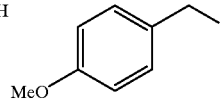 2d | 100% | 86% |
| 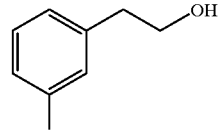 1e | 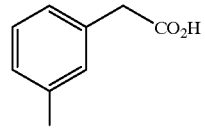 2e | 96% | <5% |
| 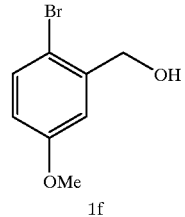 1f | 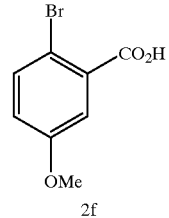 2f | 96% | 80% |
| 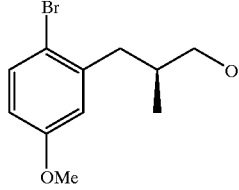 1g | 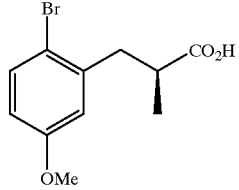 2g | 92% | 60% |
| 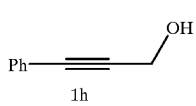 1h | 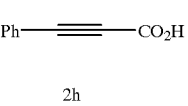 2h | 90% | 20% |
| 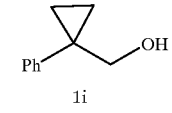 1i | 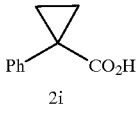 2i | 95% | — |

TABLE 1-continued

TEMPO Catalyzed Oxidation of Primary Alcohols to Carboxylic Acids

| Substrate | Product | Yield (NaClO)$_2$ | Yield (NaClO) |
|---|---|---|---|
| 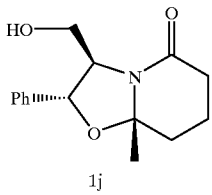 1j | 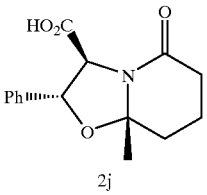 2j | 95% | — |
| 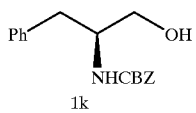 1k | 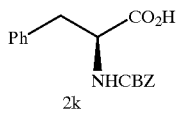 2k | 85% | — |
| 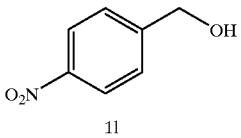 1l | 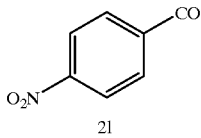 2l | 100% | — |

In conclusion, an efficient and environmentally benign procedure for the oxidation of primary alcohols to the carboxylic acids has been developed. In this procedure, NaClO$_2$ is used as the stoichiometric oxidant in the presence of catalytic amount of TEMPO and bleach (NaClO). Most primary alcohols were oxidized in essentially quantitative yield. Compared with TEMPO/NaClO/CH$_2$Cl$_2$ protocol, the amount of chlorination of electron rich aromatic rings in the substrates were dramatically reduced and the yield and purity of the products improved. Additionally, no chlorinated solvent is used.

The instant invention can be understood further by the following examples, which do not constitute a limitation of the invention.

General

All substrates and reagents were obtained commercially, except 1g (See Examples 2–5 decribing the preparation of this primary alcohol) and used without purification. $^1$H and $^{13}$C NMR spectra were recorded at 250 and 62.5 MHz respectively. The products were identified by comparing their NMR spectra with those of commercial materials except for 2g and 2j. The yields were determined by reverse phase HPLC with Zorbax SB-Phenyl or YMC ODS-AM columns and MeCN/0.1% H$_3$PO$_4$ as the mobile phase.

EXAMPLE 1

Oxidation of Primary Alcohol-TEMPO Oxidation

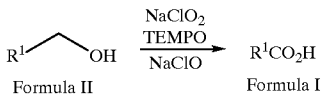

A mixture of the primary alcohol 1 (40 mmol) in MeCN (200 mL) and sodium phosphate buffer (0.67 M, pH=6.7) was heated to 35° C. TEMPO (436 mg, 2.8 mmol) was added then a solution of sodium chlorite (9.14 g 80%, 80.0 mmol in 40 mL water) and a solution of dilute bleach (1.06 mL 5.25% bleach diluted into 20 mL, 2.0 mol %) were added simultaneously in 2 hours.*

*Do not mix the sodium chlorite solution and bleach prior to the addition since the mixture appears to be unstable. The addition should be carried out as follows: approximately 20% of the sodium chlorite solution is added followed by 20% of the dilute bleach. Then the rest of the NaClO$_2$ solution and dilute bleach are added simultaneously in 2 hours. The reaction is slightly exothermic.

The mixture was stirred at 35° C. until the reaction is complete (<2 A % SM, 2–4 h) then cooled to rt. Water (300 mL) was added and the pH was adjusted to 8.0 with 2.0 N NaOH (~48 mL). The reaction was quenched by pouring into cold (0° C.) Na$_2$SO$_3$ solution (12.2 g in 200 mL water) maintained <20° C. The pH of the aqueous layer should be 8.5–9.0 After stirring for 0.5 hour at rt, MTBE (200 mL) was added with stirring. The organic layer was separated discarded. More MTBE (300 mL) was added and aqueous layer was acidified with 2.0 N HCl (~100 mL) with stirring to pH=3–4. The organic layer was washed with water (2×100 mL), brine (150 mL) to give a solution of the crude carboxylic acid 2 in 90–95% yield.

EXAMPLE 2

Preparation of 2-bromo-5-methoxybenzyl alcohol

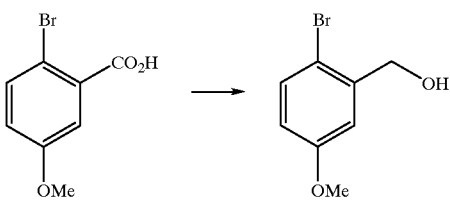

Sodium borohydride (8.6 g) is slurried in THF (150 mL KF=150 μg/mL) in a round bottom flask equipped with a thermocouple, an addition funnel, a nitrogen inlet a mechanical stirrer and a cooling bath. 2-Bromo-5-methoxybenzoic acid (50 g) is dissolved in THF (100 mL KF=150 μg/mL) is added to the sodium borohydride slurry over 45 min while maintaining the temperature at 20–25° C. The reaction must be controlled with intermittent cooling and by careful monitoring of the addition rate. The mixture is aged for 30 min at 20–25° C. Boron trifluoride etherate (36.9 g) is added over a period of 30 min at 30–35° C.

The addition of boron trifluoride etherate produces a delayed exotherm and should be added slowly in order to control the reaction temperature. The resulting white slurry is aged for 1 h at 30–35° C. and then sampled for HPLC assay. A peak at RT=8.7 min is an impurity related to the starting material. The acid is at RT=9.1 min.

The reaction mixture is cooled to 15° C. and carefully quenched into a cold (10° C.) saturated ammonium chloride solution (150 mL) while maintaining the temperature <25° C.

Ethyl acetate (500 mL) is added and the layers are separated. The organic layer is washed with water (100 mL) and then transfered to a 1L round bottom flask equipped for distillation. The solution was concentrated and charged with fresh ethyl acetate. This is repeated until a solution with a volume of 200 mL has KF<200 μg/mL. The solvent is then switched to DMF to give the final volume of 200 mL with a KF<200 μg/mL.

EXAMPLE 3

Preparation of 2-bromo-5-methoxybenzyl chloride

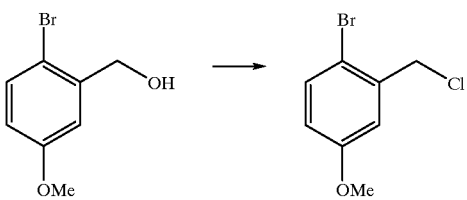

The DMF solution of the benzyl alcohol (91.3 g in 400 mL KF=300 μg/mL) is charged to a 2 L flask equipped with a mechanical stirrer, thermocouple, N₂ inlet, and cooling bath. The solution is cooled to 0–5° C. and the addition funnel is charged with thionyl chloride (55.0 g). The thionyl chloride is added over a period of 45 min while maintaining the temperture 5–10° C. The mixture is aged for 1 h at 5° C. and assayed by HPLC.

The addition funnel is charged with water (400 mL) which is added dropwise to the reaction mixture over a period of 30 min. while maintaining the temperture <15° C. The temperature is controlled by cooling and monitoring the rate of addition. The initial addition of water is highly exothermic. Using large excess of thionyl chloride results in a more exothermic quench. If the quench temperture is not controlled, hydrolysis of the benzyl chloride back to the alcohol may result.

The resulting thick white slurry is aged for 1 h at 0–5° C. The benzyl chloride is isolated by filtration. The cake is washed with (1:1) DMF:H₂O (100 mL) and then water (200 mL). The solid is dried in vacuo to give 93 g of the benzyl chloride(94% yield, 96 A %). HPLC assay: Column: Waters Symmetry C8, 4.6×250 mm; UV Detection: 220 nm; Column Temp: 25° C.; Flow rate: 1 mL/min.; Eluent: CH₃CN:H₂O:0.1% H₃PO₄ (70:30); RT (benzyl alcohol)=3.9 min; RT (benzyl chloride)=7.3 min.; and RT (DMF)=2.6 min.

EXAMPLE 4

Preparation of the Acetonide of N-propanoyl (1R, 2S)-cis-aminoindanol

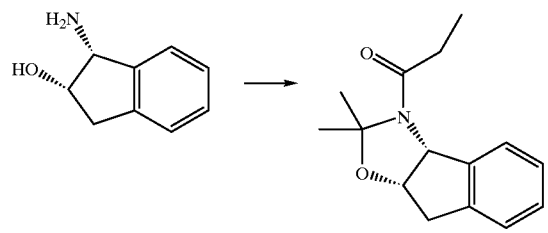

A 5 L 3-neck round bottom flask equipped with a mechanical stirrer, N₂ inlet, thermocouple probe, heating mantle, and addition funnel is charged with (1R,2S)-cis-aminoindanol (100 g), tetrahydrofuran (1.2 L, KF 120 μg/mL), and triethylamine (96 mL, KF 500 μg/mL). The resulting slurry is heated under a N₂ atmosphere to 40–45° C. giving a yellow solution. Propionyl chloride (59 mL) is charged to an addition funnel and added to the solution while maintaining the temperature at 45–50° C.

The temperature is controlled by rate of propionyl chloride addition and a cooling bath. HPLC assay shows >99% amide formed. Methanesulfonic acid (3 mL) is added to the reaction slurry. 2-Methoxypropene (140 mL) is charged to an addition funnel and added over 30 minutes at a temperature of 50° C.

The addition of 2-methoxypropene is mildly exothermic. The temperature is maintained by the rate of addition and a heating mantle. The reaction remains a slurry but does become less thick.

The reaction slurry is aged for 1–2 hours at 50° C. HPLC assay at this point shows <0.5 A % of the amide remaining. The amide is not removed in the isolation so it is important to push the reaction to completion. The reaction slurry is cooled to 0–5° C. and quenched by addition of 5% aqueous sodium carbonate solution (1 L) and heptane (1 L). The layers are stirred and separated and the organic is washed with water (300 mL).

HPLC assay at this point shows the acetonide in >98 A % and >90% yield. The acetonide/THF/heptane solution is filtered into a 2 L round bottom flask and the solution is distilled to a final volume of 700 mL. Heptane (1L) is added and the solution is distilled to a final volume of 700 mL. The distillation is done under partial vacuum at ~50° C. NMR assay at this point shows <2 mol % THF. The solution is allowed to cool and is seeded with acetonide at 35–40° C. The thick slurry is aged for 1 hour at ambient temperature then cooled to 0–5° C. and aged for 1 hour. The slurry is filtered and the cake is washed with cold heptane (200 mL) and air dried to yield acetonide as a crystalline white solid (141.1 g, 85% yield, 99.6 A %).

EXAMPLE 5

Alkylation of the Acetonide with 2-bromo-5-methoxybenzyl chloride.

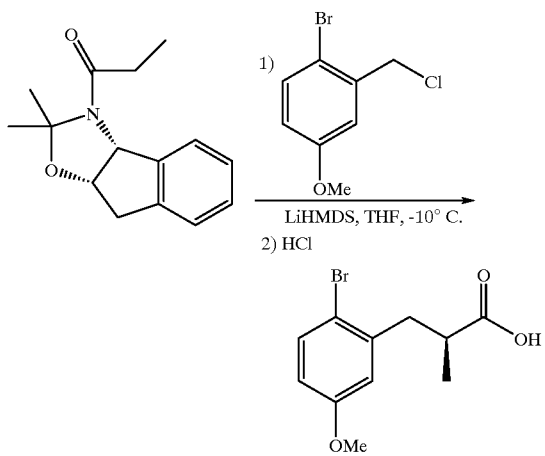

A THF solution (2L, KF<200 μg/mL) of the acetonide (252 g) and the benzyl chloride (255 g) is cooled to −10° C. Lithium bis(trimethylsilyl)amide (1.45 L) is added dropwise over 5 h at 0–2° C. The mixture is then aged for 1.5 h and assayed by HPLC.

The reaction is quenched by adding aqueous saturated ammonium chloride solution (1 L). The initial addition of the ammonium chloride should be slow in order to control the foaming. The rate can be increased when the foaming subsides.

The quenched reaction is then transfered into a mixture of aqueous ammonium chloride (1.5 L), water (0.5 L), and ethyl acetate (3 L). The mixture is then agitated for 15 min and the layers are separated. The organic layer is washed with water (1 L) and brine (0.5 L). The ethyl acetate solution is concentrated to a low volume and solvent switched to 1,4-dioxane. The dioxane solution is adjusted to a final volume of 1.8 L.

The dioxane solution of the coupled product is charged to a 12 L round bottom flask and 6 M HCl (1.5 L) is charged. The mixture is heated to reflux and monitored by HPLC.

The mixture is cooled to 20° C. and MTBE (3 L) is added. The mixture is agitated for 15 min and the layers are separated. The organic layer is washed with water (1 L). The MTBE solution of the crude acid is extracted with 0.6 M sodium hydroxide (2 L). The aqueous solution of the sodium salt of the acid is combined with MTBE (2.5 L) and cooled to 10° C.

The two phase mixture is acidified with 5.4 M sulfuric acid (250 mL), agitated for 15 min, settled and the layers separated. The MTBE solution of the acid is washed with water (0.5 L). The MTBE solution of the acid is dried by distillation and then solvent switched to THF. The final volume of the THF is 2 L with a KF<250 μg/mL. HPLC assay: column: Waters Symmetry; Eluent: acetonitrile: water: phosphoric acid (70:30:0.1); Flow rate: 1 mL/min.; RT (acetonide)=4.5 min.; RT (benzyl chloride)=7.5 min.; RT (coupled product)=11.5 min.; RT (aminondanol)=1.7 min.; RT (hydroxyamide)=1.7 min.; and RT (acid)=4.5 min.

EXAMPLE 6

Preparation of 3-(2-bromo-5-methoxyphenyl)-2-methylpropanol

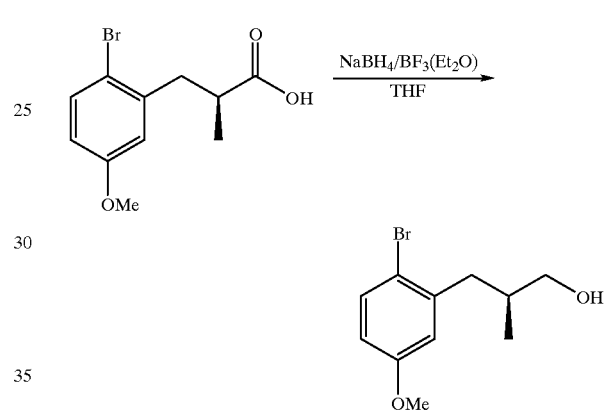

Sodium borohydride (33 g) is slurried in THF (0.5 L KF=200 μg/mL) in a round bottom flask. The THF solution (2 L) of the acid is added to the sodium borohydride slurry over 1 h while maintaining the temperature at 20–25° C.

The reaction is controlled with a cooling bath and by carefully monitoring the addition rate. A nitrogen sweep and proper venting of the hydrogen is also important.

The mixture is aged for 30 min at 20–25° C. Boron trifluoride etherate (152 g) is added over 1 h at 30–35° C. The addition produces a delayed exotherm and should be carefully monitored in order to control the reaction temperature. The resulting milky white slurry is aged for 1 h at 30° C. and sampled for HPLC assay.

The reaction mixture is cooled to 15° C. and carefully quenched in a cold (10° C.) ammonium chloride solution (1.5 L) while maintaing the temperature at 25° C. The rate of hydrogen evolution is controlled by the rate of the addition of the mixture into the ammonium chloride. The quenched mixture is distilled in vacuo to remove the THF. The aqueous layer is extracted with MTBE (1.5 L) and the organic layer is dried by flushing with additional MTBE. The MTBE solution is then solvent switched to hexanes and adjusted to a volume of 350 mL and seeded. The slurry is aged for 2 h at 20° C. and then cooled to 0–5° C. aged for 1 h and filtered. The cake is washed with cold hexanes (200 mL). The solid is dried under a nitrogen sweep. The isolated solid (164 g) is >99 A % by HPLC and >99%ee. HPLC: Column: Waters Symmetry C8; Solvent: acetonitrile:water: phosphoric acid (50:50:0.1); Flow rate: 1mL/min.; Detection: 220 nm; RT (acid)=10.2 min.; RT (alcohol)=10.7 min. Chiral HPLC: Column: Chiracel OD-H; Hexane:2-propanol (97:3); Flow rate: 1 mL/min.; Detection: 220 nm; RT minor isomer=21 min.; and RT major isomer=23 min.

EXAMPLE 7

Preparation of 3-(2-bromo-5-methoxyphenyl)-2-methylpropanoic acid

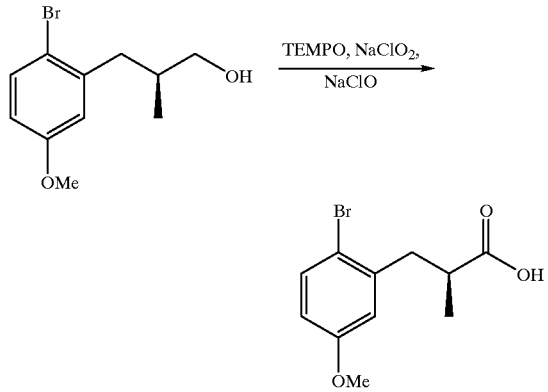

The acid was prepared following the general procedure recited in Example 1.

2g: $^1$H NMR (CDCl$_3$) δ: 7.44 (d, J=8.7 Hz, 1H), 6.78 (d, J=3.1 Hz, 1H), 6.66 (dd, J=8.7, 3.1 Hz, 1H), 3.75 (s, 3H), 3.13 (dd, J=13.1, 6.8 Hz, 1H), 2.98–2.84 (m, 1H), 2.77 (dd, J=13.1, 7.4 Hz, 1H), 1.23 (d, J=6.9 Hz, 3H).

2j: $^1$H NMR (CDCl$_3$) δ: 9.0–8.0 (broad, 1 H), 7.47–7.30 (m, 5H), 5.71 (d, J=7.7 Hz, 1H), 4.43 (d, J=7.7 Hz, 1H), 2.70–2.40 (m, 2H), 2.33–2.27 (m, 1H), 2.17–1.80 (m, 3H), 1.58 (s, 3H).

$^{13}$C NMR (CDCl$_3$) δ: 172.04, 169.48, 137.52, 128.73, 126.16, 94.66, 77.05, 64.34, 34.52, 29.91, 23.45, 17.28.

Anal. Calcd for C$_{15}$H$_{17}$NO$_4$: C, 65.44; H, 6.22; N, 5.09. Found C, 65.31; H, 6.15; N, 4.98.

What is claimed is:

1. A process for preparing a compound of Formula I:

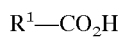

I wherein:
R$^1$ is:
a) H,
b) C$_1$–C$_8$ alkyl,
c) C$_2$–C$_8$ alkynyl,
d) C$_3$–C$_7$ cycloalkyl,
e) aryl,
f) heteroaryl, or
g) heterocyclyl;
  C$_1$–C$_8$ alkoxy, C$_1$–C$_8$ alkyl, C$_2$–C$_8$ alkynyl, or C$_3$–C$_8$ cycloalkyl, are unsubstituted or substituted with one, two or three substituents selected from the group consisting of: OH, CO$_2$R$^4$, Br, Cl, F, I, CF$_3$, C$_1$–C$_8$ alkoxy, C$_3$–C$_8$ cycloalkyl, aryl, heteroaryl, heterocyclyl, and CO(CH$_2$)$_n$CH$_3$, aryl is defined as phenyl or naphthyl, which is unsubstituted or substituted with one, two or three substituents selected from the group consisting of: OH, CO$_2$R$^4$, Br, Cl, F, I, CF$_3$, C$_1$–C$_8$ alkoxy, C$_1$–C$_8$ alkyl, C$_2$–C$_8$ alkynyl, or C$_3$–C$_8$ cycloalkyl, CO(CH$_2$)$_n$CH$_3$, or when aryl is substituted on adjacent carbons they can form a 5- or 6-membered fused ring having one, two or three heteroatoms selected from O, N, and S, this ring is unsubstituted or substituted on carbon or nitrogen with one, two or three substituents selected from the group consisting of: OH, CO$_2$R$^4$, Br, Cl, F, I, CF$_3$, C$_1$–C$_8$ alkoxy, C$_1$–C$_8$ alkyl, C$_2$–C$_8$ alkenyl, C$_2$–C$_8$ alkynyl, C$_3$–C$_8$ cycloalkyl, and CO(CH$_2$)$_n$CH$_3$;

heteroaryl is defined as a 5- or 6-membered aromatic ring containing 1, 2 or 3 heteroatoms selected from O, N and S, which is unsubstituted or substituted with one, two or three substituents selected from the group consisting of: OH, CO$_2$R$^4$, Br, Cl, F, I, CF$_3$, C$_1$–C$_8$ alkoxy, C$_1$–C$_8$ alkyl, C$_2$–C$_8$ alkynyl, C$_3$–C$_8$ cycloalkyl, CO(CH$_2$)$_n$CH$_3$, and additionally the 5- or 6-membered aromatic ring can be benzofused and unsubstituted or substituted with one, two or three substituents as described above;

heterocyclyl is defined as a 5- or 6-membered, non-aromatic ring containing 1, 2 or 3 heteroatoms selected from O, N and S, which may contain one or two double bonds and which is unsubstituted or substituted with one, two or three substituents selected from the group consisting of: OH, CO$_2$R$^4$, Br, Cl, F, I, CF$_3$, C$_1$–C$_8$ alkoxy, C$_1$–C$_8$ alkyl, C$_2$–C$_8$ alkynyl, C$_3$–C$_8$ cycloalkyl, CO(CH$_2$)$_n$CH$_3$, and additionally the 5- or 6-membered ring can be benzofused and unsubstituted or substituted with one, two or three substituents as described above;

n is: 0 to 5;
t is: 0, 1 or 2;
R$^4$ is: H, or C$_1$–C$_8$ alkyl; or
comprising the following steps:
  1) adding to a compound of Formula II in a solvent,

II solution of phosphate buffer to maintain a pH of about 4.0 to about 8.0;
  2) maintaining the phosphate-buffered biphasic mixture of the compound of Formula II at about 0° C. to about 50° C.;
  3) adding a catalytic amount of TEMPO to the mixture; and
  4) charging the TEMPO/phosphate-buffered biphasic mixture with a solution of sodium chlorite and a catalytic amount of sodium hypochlorite to oxidize to the compound of Formula I.

2. The process as recited in claim 1, wherein the solvent is selected from the group consisting of: acetonitrile, tetrahydrofuran, diethyl ether, MTBE (methyl t-butyl ether), DME (dimethoxyethane), DIGLYME (2-methoxyethyl ether), TRIGLYME (triethylene glycol dimethyl ether), toluene, benzene, hexane, pentane, dioxane, or a mixture of said solvents, including a mixture of said solvents with water.

3. The process as recited in claim 2, wherein the phosphate buffer comprises an aqueous mixture of NaOH, KOH, NaH$_2$PO$_4$, KH$_2$PO$_4$, Na$_2$HPO$_4$, and K$_2$HPO$_4$, sufficient to maintain a pH of about 4.0 to about 8.0.

4. The process as recited in claim 3, wherein TEMPO (2,2,6,6-tetramethyl-1-piperidinyloxy, free radical) is used in about 1.0 to about 10.0 mole percent.

5. The process as recited in claim 4, wherein sodium chlorite is used in about 1.0 to about 3.0 equivalents.

6. The process as recited in claim 5, wherein sodium hypochlorite is used in about 1.0 to about 7.0 mole percent.

7. The process as recited in claim 6, wherein the reaction temperature is about 0° C. to about 50° C.

8. The process as recited in claim 7, wherein the phosphate buffer comprises an aqueous mixtureof NaOH, KOH, $NaH_2PO_4$, $K_2PO_4$, $Na_2HPO_4$, and $K_2HPO_4$, sufficient to maintain a pH of about 6.5 to about 7.0.

9. The process as recited claim 8, wherein TEMPO (2,2,6,6-tetramethyl-1-piperidinyloxy, free radical) is used in about 5.0 to about 7.0 mole percent.

10. The process as recited in claim 9, wherein sodium chlorite is used in about 2.0 equivalents relative to the compound of Formula II.

11. The process as recited in claim 10, wherein sodium hypochlorite is used in about 2.0 to about 5.0 mole percent.

12. The process as recited in claim 11, wherein the reaction temperature is about 35° C. to about 40° C.

13. The process as recited in claim 12, wherein the reaction time is about 2 hours to about 4 hours.

* * * * *